United States Patent
Swenson et al.

(10) Patent No.: US 10,507,298 B2
(45) Date of Patent: Dec. 17, 2019

(54) RESPIRATION MASK AND SEAL THEREFOR

(71) Applicants: Orel Yehuda Swenson, Annapolis, MD (US); Brian Patrick Anderson, Skaneateles, NY (US)

(72) Inventors: Orel Yehuda Swenson, Annapolis, MD (US); Brian Patrick Anderson, Skaneateles, NY (US)

( * ) Notice: Subject to any disclaimer, the term of this patent is extended or adjusted under 35 U.S.C. 154(b) by 0 days.

(21) Appl. No.: 15/642,046

(22) Filed: Jul. 5, 2017

(65) Prior Publication Data
US 2019/0009044 A1 Jan. 10, 2019

(51) Int. Cl.
*A61M 16/06* (2006.01)
*A61M 16/00* (2006.01)
*A61M 16/01* (2006.01)
*A61M 16/10* (2006.01)

(52) U.S. Cl.
CPC .... *A61M 16/0605* (2014.02); *A61M 16/0084* (2014.02); *A61M 16/06* (2013.01); *A61M 16/0078* (2013.01); *A61M 16/01* (2013.01); *A61M 16/1005* (2014.02); *A61M 2016/0661* (2013.01)

(58) Field of Classification Search
CPC .............. A61M 16/00; A61M 16/0078; A61M 16/0084; A61M 16/0048; A61M 16/06; A61M 16/0605; A61M 16/0611; A61M 16/0616; A61M 16/0622; A61M 2016/0661; A62B 18/00; A62B 18/02; A62B 18/025; A62B 18/06
See application file for complete search history.

(56) References Cited

U.S. PATENT DOCUMENTS

| | | | | |
|---|---|---|---|---|
| 2004/0107968 A1* | 6/2004 | Griffiths | ............... | A62B 18/025 128/206.21 |
| 2004/0182398 A1* | 9/2004 | Sprinkle | ............... | A61M 16/06 128/207.13 |
| 2006/0096598 A1* | 5/2006 | Ho | ......... | A61M 16/06 128/206.24 |
| 2012/0067349 A1* | 3/2012 | Barlow | ................. | A61M 16/06 128/205.25 |
| 2012/0318272 A1* | 12/2012 | Ho | ......... | A61M 16/06 128/205.25 |
| 2013/0014760 A1* | 1/2013 | Matula, Jr. | ............ | A61M 16/06 128/205.25 |

(Continued)

OTHER PUBLICATIONS

Lexan (Polycarbonate) Dielectric Corporation, Aug. 16, 2012, www.dielectriccorp.com/downloads/thermoplastics/lexan.pdf.*

*Primary Examiner* — Colin W Stuart
(74) *Attorney, Agent, or Firm* — Wiley Rein LLP

(57) ABSTRACT

A respiration mask includes an upper portion connectible to a source of gas, a lower portion connected to the upper portion, facilitating a seal between the upper portion and a person's face, and a deformation element incorporated into the lower portion to establish a plurality of sealing barriers between the lower portion and the person's face. The upper portion is made from a first material with a modulus of elasticity between 150 ksi and 200,000 ksi. The deformation element is made from a second material exhibiting a hardness below one of 40 Shore A or 80 Shore OO and tear a resistance greater than 5 lbf/in.

14 Claims, 8 Drawing Sheets

(56) References Cited

U.S. PATENT DOCUMENTS

2015/0013682 A1\* 1/2015 Hendriks .............. A61M 16/06
   128/206.24
2015/0040909 A1\* 2/2015 Willard ................ A61M 16/06
   128/205.25

\* cited by examiner

RESPIRATION MASK AND SEAL THEREFOR

CROSS-REFERENCE TO RELATED APPLICATION(S)

This U.S. Patent Application is a first-filed patent application and does not rely for priority on any other patent application.

FIELD OF THE INVENTION

The present disclosure concerns a respiration mask. More particularly, the present disclosure provides a respiration mask providing a seal with a person's face that is improved over respiration masks in the prior art. Even more specifically, the present disclosure encompasses an enhanced seal for a respiration mask.

DESCRIPTION OF THE BACKGROUND AND RELATED ART

As should be apparent to those skilled in the construction of respiration masks, the ability to create an effective seal between a respiration mask and a person's face improves the performance of the respiration mask.

Respiration masks may be used in connection with resuscitators that are employed by medical technicians including, for example, emergency medical technicians, hospital personnel, and doctors. Resuscitators typically are connected to elastic bags that may be compressed to force air into a person's lungs, assisting with respiration. As should be apparent, a suitable seal between the mask and the person's face increases the ability of the resuscitator to perform its function.

As should be apparent to those who use resuscitators, the mask may not provide a suitable seal under certain circumstances. To compensate, a medical technician may be required to press the mask more forcefully against the person's face. However, this may prove to be awkward for the medical technician and, therefore, may impede the medical technician's ability to attend to the person's medical needs. Still further, resuscitators may require multiple medical technicians to cooperate together for effective operation of the device.

While the prior art provides a number of constructions for respiration masks, respiration masks continue to suffer from one or more deficiencies in design and construction that undermine the mask's ability to provide an optimal seal with a person's face.

The prior art does not provide suitable solutions to one or more of the difficulties enumerated above.

SUMMARY OF THE INVENTION

The present disclosure addresses one or more of the deficiencies with respect to the prior art.

In particular, the present disclosure provides for a respiration mask that includes an upper portion connectible to a source of gas, a lower portion connected to the upper portion, facilitating a seal between the upper portion and a person's face, and a deformation element incorporated into the lower portion to establish a plurality of sealing barriers between the lower portion and the person's face. The upper portion is made from a first material with a modulus of elasticity between 150 ksi and 200,000 ksi. The deformation element comprises second material exhibiting a hardness below one of 40 Shore A or 80 Shore OO and tear a resistance greater than 5 lbf/in.

In one embodiment, the second material further exhibits an elongation of ≥110% between an initial condition and a break condition.

In another embodiment, the second material is an elastomer.

Still further, the first material may be a plastic.

The present invention also provides for a respiration mask where the seal facilitates transfer of gas including at least one of air, oxygen, and anesthesia.

It is contemplated that the upper portion may include flexure elements to facilitate flexure of the upper portion, thereby assisting the lower portion to transfer gas to the person.

It is contemplated that the flexure elements may be slits cut into the upper portion.

Alternatively, the flexure elements may be ribs incorporated into the upper portion.

It is contemplated that the plurality of sealing barriers discourages egress of the gas between the lower portion and the person's face.

In one embodiment, the deformation element includes a first sealing barrier disposed within the upper portion at a position above a bottom edge of the upper portion, and a second sealing barrier disposed on the bottom edge of the upper portion.

In another embodiment, the deformation element includes a flange portion connected to a bottom edge of the upper portion, and three sealing barriers, separated by gaps, extending downwardly from the flange portion.

Still further, the deformation element may include a flexible body with a triangular cross-section having an outer sloped surface and an inner sloped surface.

In this embodiment, the deformation element also may have an internal rib connected to a bottom edge of the upper portion.

A flange may be connected at a proximal end to the bottom edge of the upper portion, extending downwardly and outwardly from the bottom edge of the upper portion to a distal end.

It is contemplated that the flange will be made from the first material.

In another embodiment, the internal rib may connect to the bottom edge of the upper portion at a first end and extend to a second end, the outer sloped surface may extend from the second end to a third end, the inner sloped surface may extend from the second end to a fourth end, and the third end may connect to the distal end of the flange.

It is contemplated that the respiration mask may include a deformation element that has a flange portion and a plurality of protrusions extending downwardly from the flange portion.

The plurality of protrusions may be cylindrically-shaped.

The plurality of protrusions may be separated from one another by gaps. Further aspects of the present invention will be made apparent from the paragraphs that follow.

BRIEF DESCRIPTION OF THE DRAWING(S)

The present invention will now be described in connection with the drawings appended hereto, in which.

DETAILED DESCRIPTION OF EMBODIMENT(S) OF THE INVENTION

The present disclosure is now provided in connection with one or more embodiments. The discussion of specific embodiments is not intended to be limiting of any aspect of the instant disclosure. To the contrary, the discussion of the embodiments is intended to exemplify the breadth and scope of this patent application. As should be apparent to those skilled in the art, variations and equivalents of the embodiment(s) described herein may be employed without departing from the scope of the present disclosure. Those variations and equivalents are intended to be encompassed by the scope of the present patent application.

Figure 1:
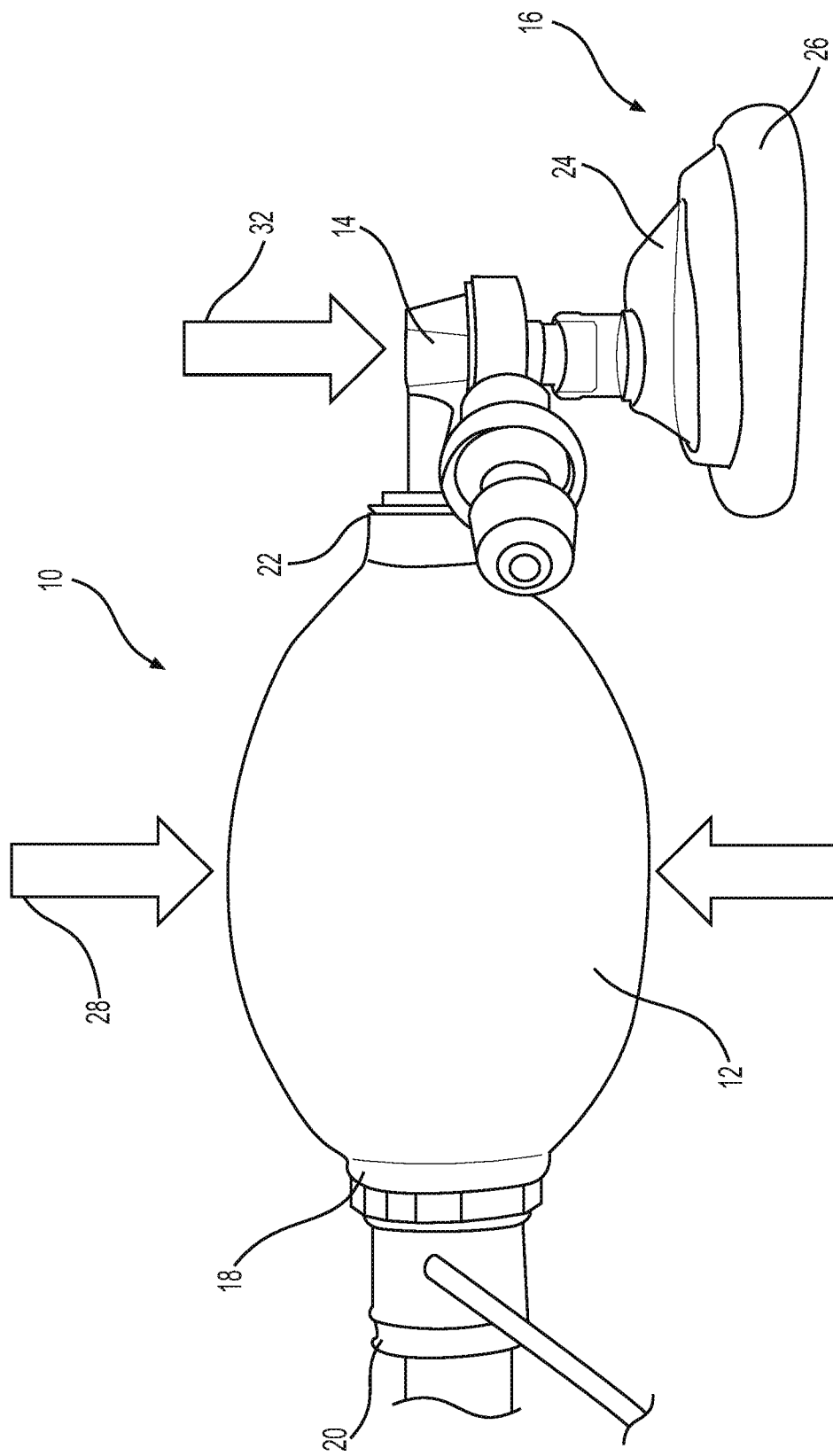
FIG. 1 is a side view illustration of one example of a manual resuscitator known to those skilled in the art.

FIG. 1 is a side view of a resuscitator 10 of the type known in the prior art. The resuscitator 10 includes a flexible bag 12, a connector 14, and a respiration mask 16. At a distal end 18, the flexible bag 12 includes a connector 20 that permits air to be drawn into the flexible bag 12. The proximal end 22 of the flexible bag 12 attaches to the connector 14. In the illustrated embodiment, the connector 14 is an L-shaped pipe that connects the flexible bag 12 to the respiration mask 16.

The respiration mask 16 includes an upper portion 24 and a lower portion 26. The upper portion 24 is made from a transparent material such as plastic. The lower portion 26 is made from a transparent, rubber-like material.

As should be apparent to those skilled in the art, when the resuscitator 10 is used, the medical technician repeatedly squeezes the flexible bag 12 in the direction of the arrows 28, 30, simulating respiration. By squeezing the flexible bag 12, air is forced through the respiration mask 16, into the person's lungs. Upon release of the flexible bag 12, the person is permitted to exhale. When the bag is released, the flexible bag 12 returns to its original state, refilling with air prior to a subsequent compression.

To maintain a seal between the respiration mask 16 and the person's face, the medical technician typically applies a force, in the direction of the arrow 32, to gently press the respiration mask 16 against the person's face.

As should be apparent to those skilled in the art, the amount of force required to establish a suitable seal with a person's face varies from one person to another, depending on a number of variables. For example, the size and shape of the person's face can affect the quality of the seal with the respiration mask 16.

As also should be apparent to those skilled in the art, the use of the resuscitator 10 is a two-handed operation. Typically, with one hand, the medical technician applies downward pressure, in the direction of the arrow 32, to press the respiration mask 16 against the person's face. With the other hand, the medical technician applies repetitive pressure, in the direction of the arrows 28, 30, to assist with the person's respiration.

In some instances, the force required to establish a suitable seal requires that at least two medical technicians cooperate with one another when operating the resuscitator 10.

The present disclosure describes several embodiments that improve upon the prior art respiration mask 16. In particular, the present disclosure provides several embodiments of a respiration mask that benefit, inter alia, from the application of less pressure (applied in the direction of the arrow 32) to establish a suitable seal between the respiration mask 16 and a person's face.

Figure 2:
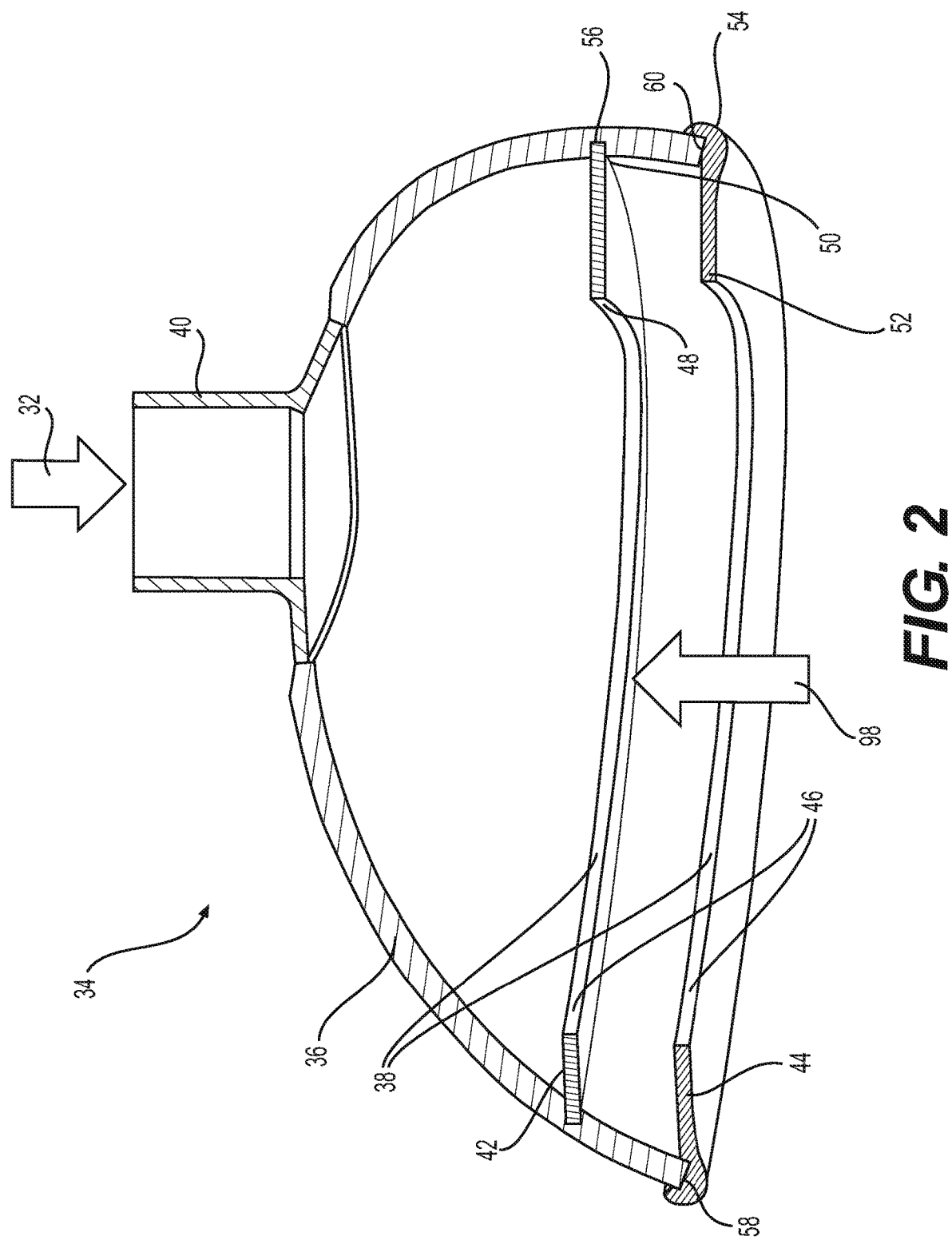
FIG. 2 is a cross-sectional side view of a first embodiment of a respiration mask according to the present disclosure.

FIG. 2 illustrates a first embodiment of a respiration mask 34 consistent with the present disclosure.

The respiration mask 34 includes an upper portion 36 and a lower portion 38. Together, the upper portion 36 and the lower portion 38 cooperate to assist with delivery of a gas to a person.

It is noted that the respiration mask 34 may be constructed from a larger or fewer number of parts than the upper portion 36 and the lower portion 38 without departing from the present disclosure.

The respiration mask 34 is contemplated for use in a variety of circumstances. For example, the respiration mask 34 may be used as a part of the resuscitator 10, being substituted for the respiration mask 16 illustrated in FIG. 1. In another example, the respiration mask 34 may be used to deliver oxygen to a person from a supplemental oxygen tank. Still further, the respiration mask 34 may be used in an operating theater to provide anesthesia to a person. As such, the respiration mask 34, together with the other embodiments described herein, should not be understood to be limited to use with the resuscitator 10. The respiration mask 34 may be employed in any alternative environment without departing from the scope of the present invention.

The upper portion 36 is connectible to a source of gas via a connector 40. Without limiting the scope of the present disclosure, the gas may include air, oxygen, anesthesia, and the like. The source of gas may be air provided by a flexible bag 12. Still further, the gas may be provided from a gas cylinder or gas generator, as should be apparent to those skilled in the art.

The lower portion 38 of the respiration mask 34 connects to the upper portion 36. In the embodiment illustrated in FIG. 1, the lower portion 38 encompasses a first sealing barrier 42 and a second sealing barrier 44, separated from one another. Together, the first sealing barrier 42 and the second sealing barrier 44 form the lower portion 38.

In this first embodiment, the first sealing barrier 42 is separate from the second sealing barrier 44. It is contemplated, however, that the first sealing barrier 42 and the second sealing barrier 44 may be connected to one another. For example, the first and second sealing barriers 42, 44 may be integrally formed with one another.

Together, the first sealing barrier 42 and the second sealing barrier 44 cooperate to form a deformation element 46 that facilitates the seal between the upper portion 36 and the person's face. The first sealing barrier 42 and the second sealing barrier 44 extend horizontally, inward from the walls of the upper portion 36.

As illustrated in FIG. 1, the first sealing barrier 42 is annularly-shaped, having a first interior edge 48 and a first exterior edge 50. Similarly, the second sealing barrier 44 is annularly-shaped with a second interior edge 52 and a second exterior edge 54. Both the first sealing barrier 42 and the second sealing barrier 44 are flexible, thereby deforming when pressed into contact with the person's face in the direction of the arrow 32. In particular, the first sealing barrier 42 and the second sealing barrier 44 deform in the direction of the arrow 98 when pressure is applied to the respiration mask 34.

The first sealing barrier 42 and the second sealing barrier 44, which cooperate to form the deformation element 46, establish a plurality of sealing barriers 42, 44 with the person's face. While two sealing barriers 42, 44 are illustrated in this embodiment, the respiration mask 34 may include a larger number of sealing barriers 42, 44 without departing from the scope of the present disclosure.

The upper portion 36 of the respiration mask 34 is contemplated to be made from a first material with a modulus of elasticity between 150 ksi and 200,000 ksi. A material having a modulus of elasticity within this range is contemplated to provide the upper portion 36 with a sufficient rigidity to maintain a dome-shaped cup above the person's nose and mouth. A modulus of elasticity between 150 ksi and 200,000 ksi also is contemplated to provide a sufficient flexibility so that the respiration mask 34 fits comfortably on the person's face.

Suitable materials for the upper portion 36 include plastics, such as polyethylene, high density polyethylene, and the like. Although plastics are contemplated to be employed in the manufacture of the upper portion 36, other materials also may be employed without departing from the scope of the present disclosure. For example, some natural materials, metals, and composite materials are contemplated to meet the elasticity requirements enumerated above. Accordingly, these materials also are encompassed by the present disclosure.

The deformation element 46 of the lower portion 38 of the respiration mask 34 is contemplated to be made from a second material, such as an elastomer exhibiting a hardness below 40 Shore A or 80 Shore OO. Alternatively, the second material may exhibit a hardness below 35 Shore A or 70 Shore OO. Still further, the second material may exhibit a hardness below 30 Shore A or 60 Shore OO.

In addition, the second material is contemplated to exhibit a tear resistance greater than 5 lbf/in. In another embodiment, the tear strength is contemplated to be greater than 10 lbf/in. In alternative embodiments, the tear strength is contemplated to be greater than 15 lbf/in, 20 lbf/in, 25 lbf/in, 30 lbf/in, or 35 lbf/in.

Still further, the second material is contemplated to exhibit an elongation of ≥110% between an initial condition and a break condition. Alternatively, the second material may exhibit an elongation of ≥120% between an initial condition and a break condition. In other contemplated embodiments, the second material may exhibit an elongation of ≥130%, ≥140%, or ≥150% between an initial condition and a break condition.

It is contemplated that, if the second material exhibits the enumerated properties, the second material will be sufficiently flexible to ensure an adequate seal with the person's face. The second material may be a solid material, an elastomer, or a foam material. Still other materials may be employed without departing from the scope of the present disclosure.

Concerning the first and second materials, it is contemplated that both may be transparent or translucent. However, opaque and semi-opaque materials also are contemplated to fall within the scope of the present disclosure.

With continued reference to FIG. 2, the first sealing barrier 42 is disposed within a groove 56 that is provided on the interior surface of the upper portion 36. The first sealing barrier 42 may be affixed within the groove 56 via a suitable fastener, such as an adhesive. Alternatively, it is contemplated that the first sealing barrier 42 may be retained within the groove 56 via an interference fit with the groove 56. Other ways to fasten the first sealing barrier 42 within the groove 56 also are contemplated to fall within the scope of the present disclosure.

In an alternative contemplated embodiment, it is contemplated that a groove 56 may not be needed. In such an embodiment, it is contemplated that the first sealing barrier 42 may be affixed directly to the upper portion 36, either by an adhesive, by another fastener, or by an interference fit. As such, the groove 56 is not required in the construction of the respiration mask 34.

The second sealing barrier 44 is contemplated to include a groove 58 therein. The groove 58 is contemplated to engage a bottom edge 60 of the upper portion 36 of the respiration mask 34. The second sealing barrier 44 may be connected to the bottom edge 60 of the upper portion 36 by a suitable fastener, such as an adhesive. Alternatively, the second sealing barrier 44 may attach to the upper portion 36 via an interference fit. Other ways to secure the second sealing barrier 44 to the bottom edge 60 of the upper portion 36 also are contemplated to fall within the scope of the present disclosure.

As noted, the first sealing barrier 42 and the second sealing barrier 44 are separated from one another by a gap and form the deformation element 46. The first sealing barrier 42 and the second sealing barrier 44 are contemplated to be made from the second material, as discussed above.

Figure 3:
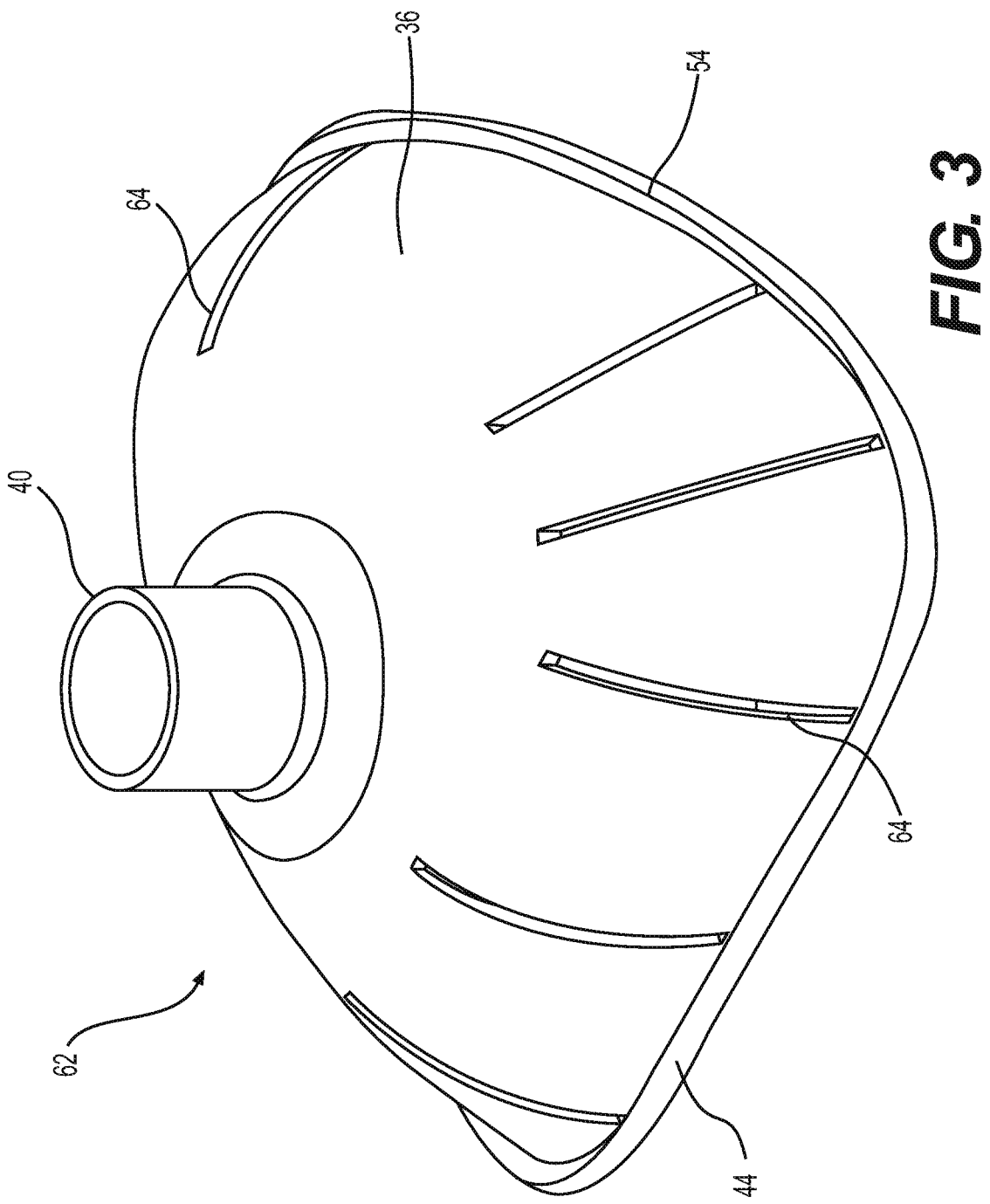
FIG. 3 is a perspective view of a second embodiment of a respiration mask consistent with the present disclosure.

FIG. 3 is a perspective illustration of a second embodiment of a respiration mask 62 according to the present disclosure. This second embodiment is a variation of the first embodiment of the respiration mask 34.

The respiration mask 62 differs from the respiration mask 34 in that the respiration mask 62 includes a plurality of slits 64 in the upper portion 36. The slits 64 act as flexure elements to alter the flexibility of the upper portion 36, which may be desirable in certain circumstances. The slits 64 are contemplated to increase the flexibility of the upper portion 36.

As should be apparent to those skilled in the art, the slits 64 are merely one type of flexure element that may be incorporated into the upper portion 36. It is contemplated, for example, that ridges may be used as flexure elements to decrease the flexibility of the upper portion 36.

The term "flexure element" is intended to refer to any element that may be used to increase or decrease the flexibility of aspects of the respiration mask 62. The flexure elements may be incorporated into any of the remaining embodiments of the respiration masks described herein.

Since the respiration mask 62 is contemplated to be the same as the respiration mask 34 except for the addition of the slits 64, the respiration mask is contemplated to include the first sealing barrier 42 and the second sealing barrier 44, incorporated therein in the manner discussed above.

Figure 4:
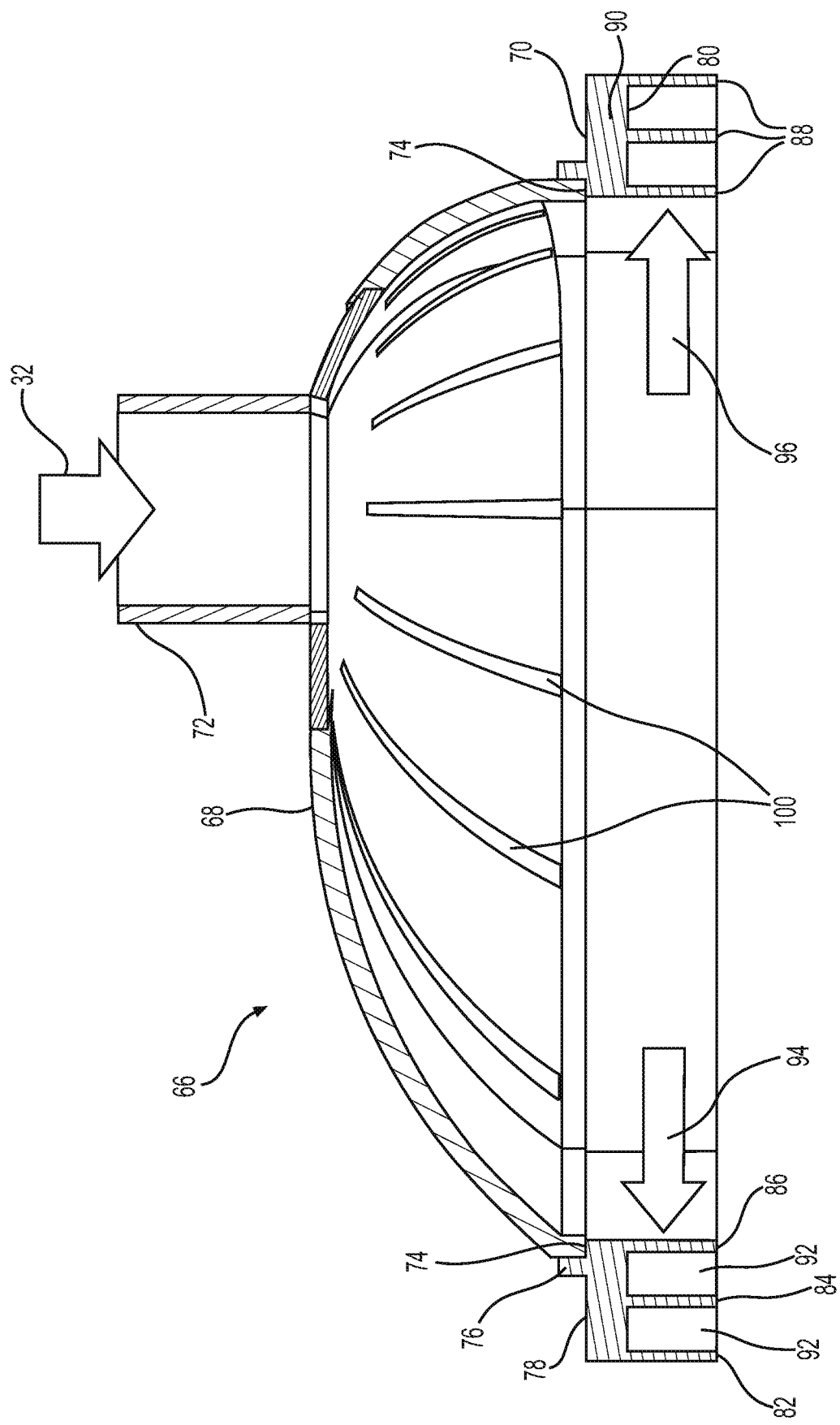
FIG. 4 is a cross-sectional side view of a third embodiment of a respiration mask incorporating the inventive aspects of the present disclosure.

FIG. 4 is a cross-sectional side view of a third embodiment of a respiration mask 66 according to the present disclosure.

The respiration mask 66 includes an upper portion 68 connected to a lower portion 70. A connector 72 attaches to the upper portion 68 so that a gas may be introduced into the respiration mask 66. The lower portion 70 is attached to a bottom edge 74 of the upper portion 68.

The lower portion 70 includes a lip 76 extending upwardly from an upper surface 78 thereof. The lip 76 extends around the upper surface 78 of the lower portion 70 and engages the periphery of the bottom edge 74 of the upper portion 68. The lip 76 helps to affix the lower portion 70 to the upper portion 68. The lip 76 also helps to establish a seal between the upper portion 68 and the lower portion 70.

The lower portion 70 is contemplated to be fastened to the bottom edge 74 of the upper portion 68. A fastener, such as an adhesive, may be employed to connect the lower portion 70 to the upper portion 68. As with the prior embodiment, the lower portion 70 may connect to the upper portion 68 via an interference fit. Still further, the lower portion 70 may connect to the upper portion 68 using any alternative fastener, as should be apparent to those skilled in the art.

The lower portion 70 defines a flange portion 90. The flange portion 90 is annularly-shaped and extends between the upper surface 78 and a lower surface 80 of the lower portion 70. A first sealing barrier 82, a second sealing barrier 84, and a third sealing barrier 86 extend downwardly from the lower surface 80 of the flange portion 90. Together, the first sealing barrier 82, the second sealing barrier 84, and the third sealing barrier 86 form a deformation element 88.

It is noted that the flange portion 90 is horizontally disposed while the first sealing barrier 82, the second sealing barrier 84, and the third sealing barrier 86 are vertically disposed. In other words, the sealing barriers 82, 84, 86 are perpendicularly disposed with respect to the flange portion 90. In an alternative construction, it is contemplated that the sealing barriers 82, 84, 86 may be disposed at an angle with respect to the flange portion 90.

The first sealing barrier 82, the second sealing barrier 84, and the third sealing barrier 86 are shaped as annular, flexible walls. As in the case of the deformation element 46 discussed in connection with the respiration mask 34, the deformation element 88 establishes a plurality of sealing barriers 82, 84, 86 that create a seal between the respiration mask 66 and the person's face so that the gas may be delivered to the person.

In this embodiment, the first sealing barrier 82, the second sealing barrier 84, and the third sealing barrier 86 are integrally formed with the flange portion 90. However, this construction is not required for the lower portion 70, as should be apparent to those skilled in the art. The first sealing barrier 82, the second sealing barrier 84, and the third sealing barrier 86 are separated by gaps 92 there between.

Like the respiration masks 34, 62, the upper portion 68 of the respiration mask 66 is contemplated to be made from the first material. The lower portion 70 of the respiration mask 66 is contemplated to be made from the second material.

As should be apparent from FIG. 4, the first sealing barrier 82, the second sealing barrier 84, and the third sealing barrier 86 are illustrated in their non-deformed condition prior to the respiration mask 66 being positioned on a person's face. When the respiration mask 66 is pressed against the person's face in the direction of the arrow 32, the first sealing barrier 82, the second sealing barrier 84, and the third sealing barrier 86 deform outwardly in the direction of the arrows 94, 96.

With renewed reference to FIG. 2, it is noted that the first sealing barrier 42 and the second sealing barrier 44 are illustrated in the non-deformed condition prior to the respiration mask 34 being pressed against a person's face. When the respiration mask 34 is applied to a person's face, the first sealing barrier 42 and the second sealing barrier 44 will deform in the direction of the arrow 98.

Returning to FIG. 4, the interior of the upper portion 68 includes a plurality of ribs 100. The ribs 100 act as flexure elements that enhance the rigidity of the upper portion 68. One or all of the ribs 100 may be replaced with slits 64 without departing from the scope of the instant disclosure.

Figure 5:
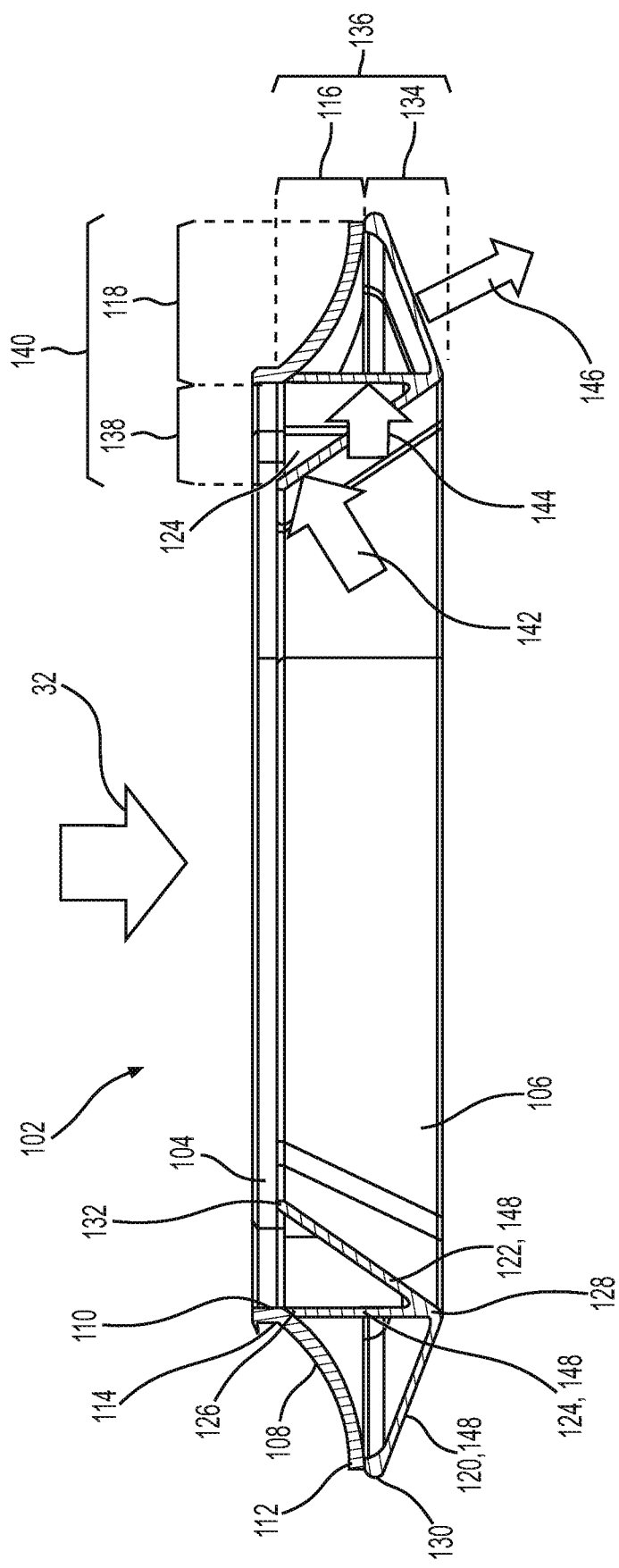
FIG. 5 is a cross-sectional, partial side view of a fourth embodiment of a respiration mask according to the present disclosure.

FIG. 5 is a cross-sectional side view of a portion of a respiration mask 102 according to a fourth embodiment. Part of an upper portion 104 is shown in this view. In addition, part of a lower portion 106 is illustrated.

The upper portion 104 is contemplated to be fabricated from the first material, as discussed above. The lower portion 106 is contemplated to be made from the second material.

In this embodiment of the respiration mask 102, a flange 108 extends outwardly and downwardly from the upper portion 104. The flange 108 is contemplated to be made from the first material and to be formed integrally as a part of the upper portion 104.

In one contemplated variation, the flange 108 may be a separate element that is connected to the upper portion 104 via a suitable fastener, such as an adhesive. In an alternative embodiment, the flange 108 may be omitted altogether.

The flange 108 is curved, extending from a proximal end 110 to a distal end 112. The proximal end 110 is adjacent to the lower edge 114 of the upper portion 104. The flange 108 extends a predetermined distance 116 downwardly and a predetermined distance 118 outwardly from the lower edge 114 of the upper portion 104. Being curved, it is contemplated that the flange 108 provides flexible support to the lower portion 106, particularly the outer sloped surface 120, which is discussed in greater detail herein.

The lower portion 106 includes three basic components that establish its triangular cross-sectional shape: an outer sloped surface 120, an inner sloped surface 122, and a reinforcing rib 124. The outer sloped surface 120 and the inner sloped surface 122 establish the triangular shape of the lower portion 106, with the reinforcing rib 124 provides internal structural support therefor.

While the lower portion 106 includes the outer sloped surface 120, the inner sloped surface 122, and the reinforcing rib 124, it is contemplated that the lower portion 106 may be constructed without the reinforcing rib 124. Still further, additional elements may be added without departing from the present disclosure.

In the embodiment illustrated in FIG. 5, the reinforcing rib 124 extends vertically downward from the lower edge 114 of the upper portion 104. The reinforcing rib 124 extends from a first end 126 to a second end 128. The outer sloped surface 120 extends from the second end 128 to a third end 130. The inner sloped surface 122 extends from the second end 128 to a fourth end 132. The third end 130 lies to one side of the reinforcing rib 124, while the fourth end 132 lies on the opposite side of the reinforcing rib 124.

It is contemplated that the first end 126 of the reinforcing rib 124 attaches to the lower edge 114 of the upper portion 104 via a suitable fastener, such as an adhesive. Similarly, it is contemplated that the third end 130 connects to the distal end 112 of the flange 108 via a suitable fastener, such as an adhesive. In alternative contemplated embodiments, the connections may be via interference fits, as required or as desired. Still other fasteners may be employed without departing from the scope of the present disclosure.

As illustrated in FIG. 5, the outer sloped surface 120 defines a predetermined height 134 and extends along the predetermined distance 118. Similarly, the inner sloped surface 122 defines a predetermined height 136 and a predetermined width 138. As should be apparent from FIG. 5, the lower portion 106 defines a total height 136 and a total width 140.

Since the entirety of the lower portion 106 is contemplated to be flexible, when a medical technician presses the respiration mask 102 in the direction of the arrow 32, the lower portion 106 is contemplated to deform in at least the directions of the arrows 142, 144, 146. However, the second material may deform in any manner other than the directions of the arrows 142, 144, 146 without departing from the scope of the instant disclosure.

As should be apparent from FIG. 5, at least the outer sloped surface 120 and the inner sloped surface 122 cooperate to form a deformation element 148. Still further, since the reinforcing rib 124 forms a part of the lower portion 106, the reinforcing rib 124 also forms a part of the deformation element 148. As discussed in connection with the other embodiments, the deformation element 148 establishes multiple sealing barriers 120, 122, 124 to effectuate a suitable seal between the respiration mask 102 and a person's face. For the illustrated embodiment, the sealing barriers are the outer sloped surface 120, the inner sloped surface 122, and the reinforcing rib 124.

Figure 6:
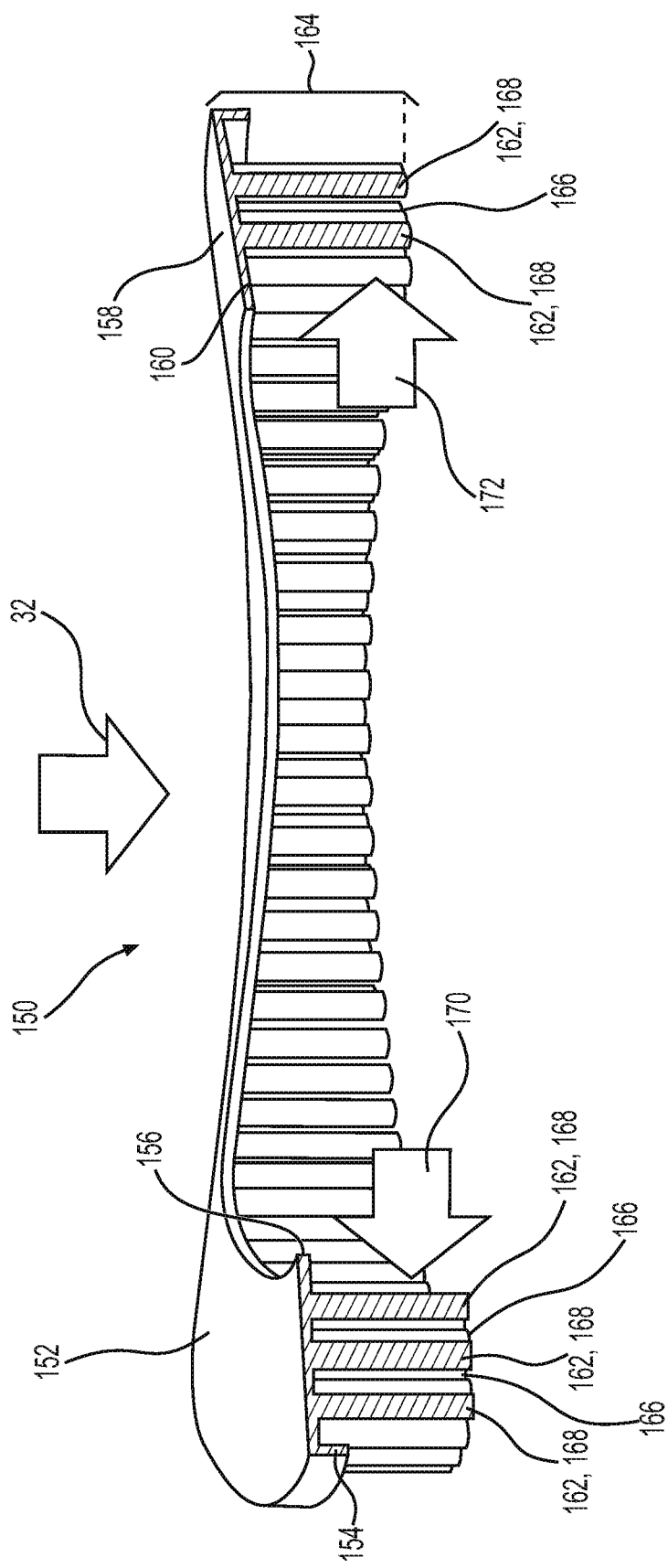
FIG. 6 is a cross-sectional side view of a fifth embodiment of a seal for a respiration mask in keeping with the present disclosure.

FIG. 6 is a cross-sectional side view of a fifth embodiment of a lower portion 150 of a respiration mask according to the present disclosure. The lower portion 150 is contemplated to attach to the bottom edge of an upper portion of a respiration mask by an adhesive or other suitable fastener, as discussed in connection with the remaining embodiments herein.

The lower portion 150 includes a flange portion 152 with an outer edge 154 and an inner edge 156. The flange portion 152 also is defined by a top surface 158 and a bottom surface 160. A plurality of finger-like protrusions 162 extend a predetermined height 164 downwardly from the bottom surface 160 of the flange portion 152. The protrusions 162 are separated from one another by gaps 166. As illustrated, the protrusions 162 are contemplated to have variable heights at different positions around the flange portion 152. All of the protrusions 162 may have the same height or different heights within the scope of the instant disclosure. Still further, the protrusions 162 may be made of different materials with differing properties to establish a suitable seal.

The protrusions 162 are contemplated to be cylindrically-shaped. However, in other contemplated embodiments, the protrusions 162 may have any other suitable shape without departing from the scope of the present disclosure.

Together, the protrusions 162 create the deformation element 168 that establishes a plurality of sealing barriers 162 between the respiration mask and the person's face. Specifically, the protrusions 162 each form a sealing barrier.

When a medical technician presses a respiration mask with the lower portion 150 against a person's face in the direction of the arrow 32, the protrusions 162 are contemplated to deform in the directions of the arrows 170, 172.

The lower portion 150 is contemplated to be made from the second material, as discussed above. The lower portion 150 is contemplated to be connected to one of the embodiments of the upper portions discussed herein.

Figure 7:
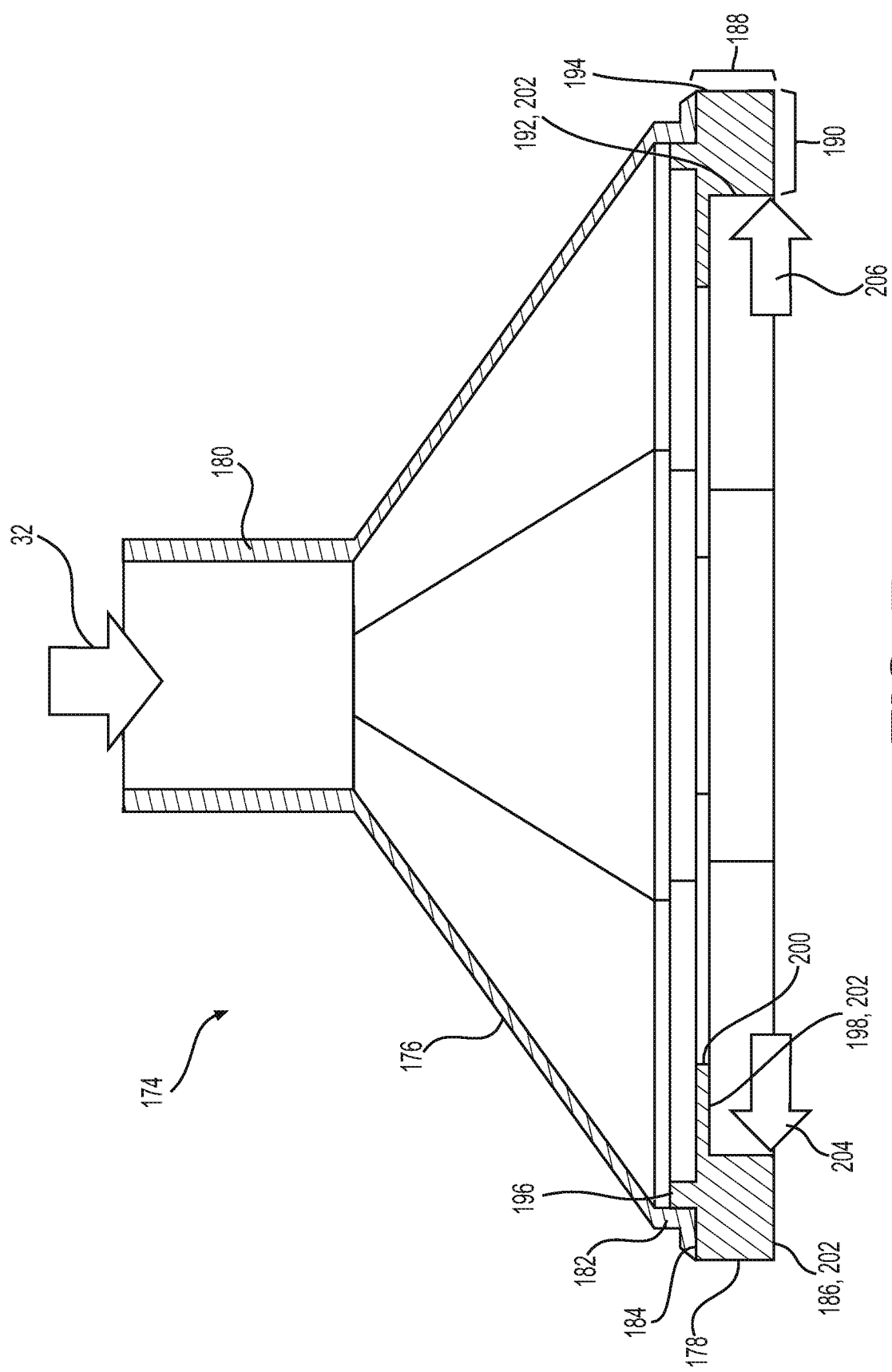
FIG. 7 is a cross-sectional side view of a sixth embodiment of a respiration mask consistent with the instant disclosure.

FIG. 7 is a cross-sectional side view of a sixth embodiment of a respiration mask 174 consistent with the instant disclosure.

In this embodiment, the respiration mask 174 includes an upper portion 176 and a lower portion 178. A connector 180 is affixed to the upper portion 176, permitting gases to be introduced into the respiration mask 174. As in prior embodiments, the upper portion is contemplated to be made from the first material. The lower portion 178 is contemplated to be made from the second material.

The upper portion 176 defines a lower edge 182 with an L-shaped cross-section. The lower edge 182 engages and is affixed to the lower portion 178. In the embodiment illustrated, the lower edge 182 is integrally formed with the upper portion 176. Accordingly, it is contemplated that the lower edge 182 will be made from the first material. However, this is not required for the construction of the respiration mask 174. It is contemplated that the lower edge 182 may be a component separate from the upper portion 176 and attached to the upper portion 176 via a suitable fastener, such as an adhesive. Still further, the lower edge 182 may be made from a material that differs from the first material and the second material without departing from the scope of the present disclosure.

The lower portion 178 defines an upper surface 184 and a lower surface 186, defining a height 188 therebetween. The lower portion 178 also defines a width 190 between an interior surface 192 and an exterior surface 194.

A lip 196 extends vertically from the upper surface 184 of the lower portion 178. The lip 196 helps to secure the lower portion 178 to the upper portion 176. The lip 196 in contemplated to be integrally formed as a part of the lower portion 178. As such, the lip 196 is contemplated to be made from the second material. In other contemplated embodiments, the lip 196 may be made from a material differing from the lower portion 178. The lip 196 also may be made from a material differing from both the first material and the second material without deviating from the present disclosure.

A flange 198 extends inwardly from the interior surface 192 to an end 200. As illustrated in FIG. 7, the flange 198 is coplanar with the upper surface 184 of the lower portion 178. Moreover, the flange 198 is contemplated to be integrally formed with the lower portion 178. As such, the flange 198 also is contemplated to be made from the second material. In other contemplated embodiments, the flange 198 may be made from a material differing from the lower portion 178. The flange 198 also may be made from a material differing from both the first material and the second material without deviating from the present disclosure.

For the respiration mask 174, at least the interior surface 192, the lower surface 186, and the flange 198 cooperate to establish the deformation element 202. Each of the interior surface 192, the lower surface 186, and the flange 198 establish barriers to discourage the egress of gases from the respiration mask 174.

As illustrated in FIG. 7, when the respiration mask 174 is pressed against a person's face, it is contemplated that the lower portion 178 will deform at least in the direction of the arrows 204, 206. As in prior embodiments, the arrows 204, 206 are merely exemplary of one possible type of deformation and, therefore, should not be understood to limit the operation and performance of the respiration mask 174.

Figure 8:
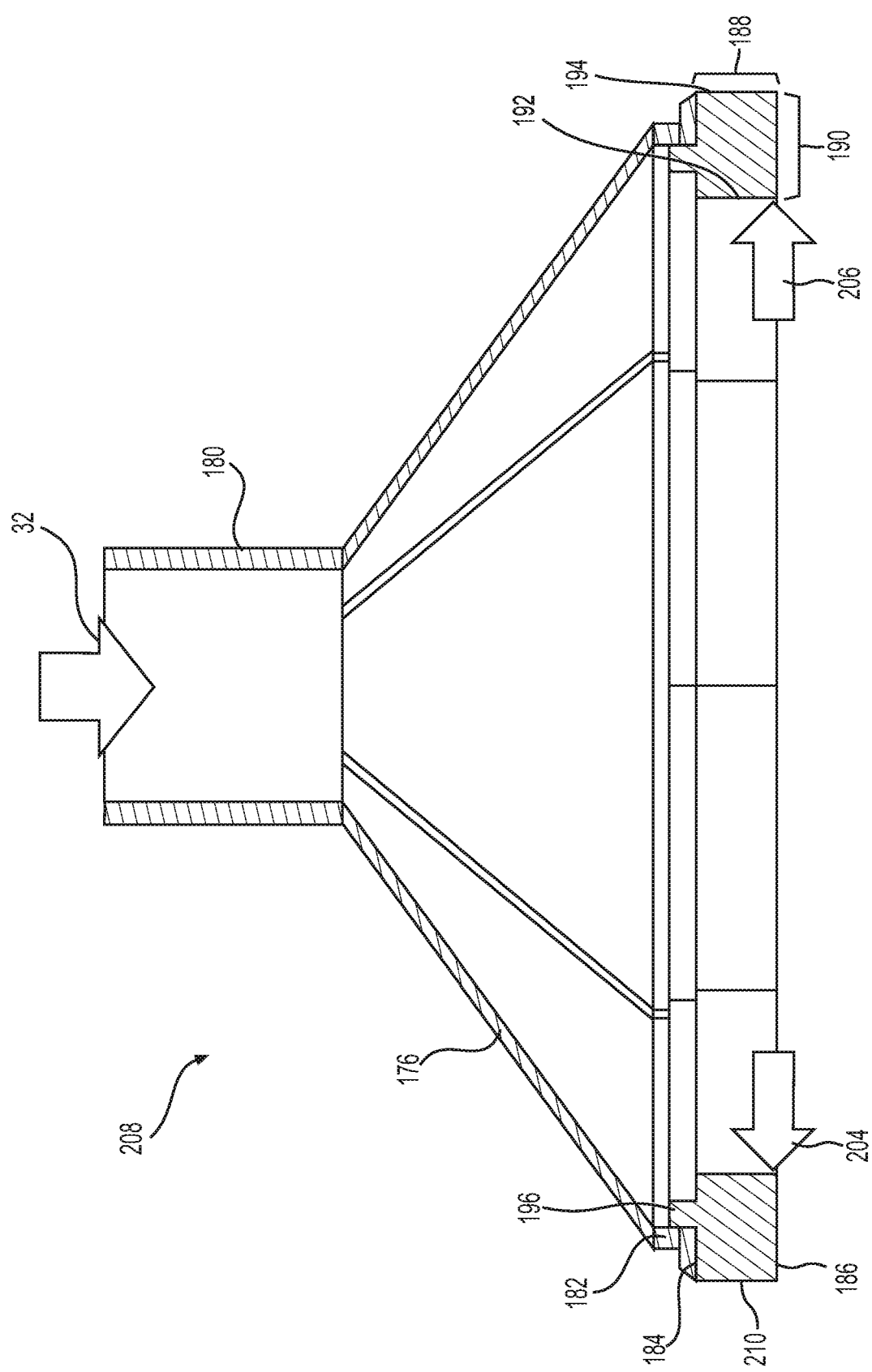
FIG. 8 is a cross-sectional side view of a seventh embodiment of a respiration mask in accordance with the present disclosure.

FIG. 8 is a cross-sectional side view of a seventh embodiment of a respiration mask 208 in accordance with the present disclosure. This embodiment is similar to the embodiment of the respiration mask 174 illustrated in FIG. 7. For the respiration mask 208, however, there is no flange 198.

It is contemplated that the respiration mask 208 will be constructed and operate in much the same manner as the respiration mask 174. In this embodiment, at least the interior surface 192 and the lower surface 186 form part of the deformation element 210 associated with the respiration mask 208.

While the embodiments of respiration masks 34, 62, 66, 102, 150, 174, 208 have been discussed in connection with assist with respiration by a resuscitator, such as the resuscitator 10, the present disclosure should not be understood to be limited solely to this use. To the contrary, the respiration masks 34, 62, 66, 102, 150, 174, 208 may be used in connection with providing air, oxygen, and/or anesthesia to a person. Still further, the respiration masks 34, 62, 66, 102, 150, 174, 208 may be employed in connection with a nebulizer. In addition, it is contemplated that the respiration masks 34, 62, 66, 102, 150, 174, 208 may be used in connection with a CPAP (Continuous Positive Airway Pressure) machine. As should be apparent, there are innumerable uses for the respiration masks 34, 62, 66, 102, 150, 174, 208 described herein and the discussion of any one particular use is not intended to limit the present disclosure.

For the various embodiments described herein, the term "fastener" has been employed. A "fastener" is any device capable of joining two part together. It is noted that "fastening" (and variants thereof) is a word intended to encompass any device or methodology be which parts are joined to one another. As discussed herein, an adhesive can join two parts together and, therefore, be a "fastener." Alternatives to fasteners include an interference fit between parts, as described. In addition, it is contemplated that parts may be joined together during manufacture, while the parts are still in a molten or semi-molten state. Still further, parts may be joined by welds. As such, the individual parts may be assembled in any manner available to those skilled in the art without departing from the present disclosure. Any discussion of one contemplated joining methodology is not intended to limit the scope of the embodiments described herein.

While not intending to be limiting of the present disclosure, it is contemplated that the deformation elements will provide a seal for a pressure up to 60 mm Hg. Alternatively, the deformation elements will provide a seal for a pressure up to 50 mm Hg. In yet another embodiment, the deformation elements will provide a seal for a pressure up to 40 mm Hg.

As noted above, the embodiment(s) described herein are intended to be exemplary of the wide breadth of the present invention. Variations and equivalents of the described embodiment(s) are intended to be encompassed by the present invention, as if described herein.

What is claimed is:

1. A respiration mask, comprising:
   an upper portion connectible to a source of gas, wherein the source of gas is adapted to provide a gas;
   a lower portion connected to the upper portion, wherein the lower portion is adapted to facilitate a leak resistant seal between the upper portion and a person's nose and mouth by surrounding the person's nose and mouth, when in use; and
   a deformation element incorporated into the lower portion comprising a flange portion, directly connected to the upper portion, and a plurality of protrusions extending downwardly from the flange portion,
   wherein a height of the plurality of protrusions is greater than a thickness of the flange portion,
   wherein the plurality of protrusions establish a plurality of sealing barriers between the lower portion and the person's nose and mouth by surrounding the person's nose and mouth, when in use,
   wherein each of the plurality of sealing barriers establishes the leak resistant seal,
   wherein the upper portion comprises a first material with a modulus of elasticity between 150 ksi and 200,000 ksi,
   wherein the deformation element comprises second material exhibiting a hardness below one of 40 Shore A or 80 Shore OO and a tear resistance greater than 5 lbf/in., and
   wherein the plurality of sealing barriers establishes the leak resistant seal for a pressure up to 60 mm Hg.

2. The respiration mask of claim 1, wherein the second material further exhibits an elongation of ≥110% between an initial condition and a break condition.

3. The respiration mask of claim 2, wherein the second material is an elastomer.

4. The respiration mask of claim 1, wherein the first material is a plastic.

5. The respiration mask of claim 1, wherein the seal facilitates transfer of gas including at least one of air, oxygen, and an anesthesia inducing gas.

6. The respiration mask of claim 1, wherein the upper portion comprises flexure elements to facilitate flexure of the upper portion, thereby assisting the lower portion to transfer gas to the person.

7. The respiration mask of claim 6, wherein the flexure elements comprise slits cut into the upper portion.

8. The respiration mask of claim 6, wherein the flexure elements comprise ribs incorporated into the upper portion.

9. The respiration mask of claim 7, wherein the flexure elements also comprise ribs incorporated into the upper portion.

10. The respiration mask of claim 1, wherein the plurality of sealing barriers is adapted to discourage egress of the gas between the lower portion and the person's face.

11. The respiration mask of claim 1, wherein each of the plurality of protrusions is cylindrically-shaped.

12. The respiration mask of claim 11, wherein each of the plurality of protrusions is separated from one another by gaps.

13. The respiration mask of claim 1, wherein the plurality of sealing barriers establishes the leak resistant seal for a pressure up to 50 mm Hg.

14. The respiration mask of claim 1, wherein the plurality of sealing barriers establishes the leak resistant seal for a pressure up to 40 mm Hg.

* * * * *